United States Patent [19]
Whitton et al.

[11] Patent Number: 6,162,916
[45] Date of Patent: Dec. 19, 2000

[54] PROCESS FOR THE PREPARATION OF PYRIMIDINE COMPOUNDS

[75] Inventors: Alan John Whitton, Falkirk; Brian Geoffrey Cox, Ponynton; Gareth Andrew De Boos, Ramsbottom; Ian Gordon Berry, Manchester; Ian George Fleming, Grangemouth; Raymond Vincent Heavon Jones, West Lothian, all of United Kingdom

[73] Assignee: Zeneca Limited, United Kingdom

[21] Appl. No.: 09/242,429

[22] PCT Filed: Jul. 25, 1997

[86] PCT No.: PCT/GB97/02015

§ 371 Date: Feb. 16, 1999

§ 102(e) Date: Feb. 16, 1999

[87] PCT Pub. No.: WO98/07707

PCT Pub. Date: Feb. 26, 1998

[30] Foreign Application Priority Data

Aug. 19, 1996 [GB] United Kingdom ............. 9617351

[51] Int. Cl.$^7$ ................................. C07D 239/34
[52] U.S. Cl. ............................................. 544/319
[58] Field of Search ............................... 544/319

[56] References Cited

U.S. PATENT DOCUMENTS 5,773,445  6/1998  Gayer ........................... 544/319

FOREIGN PATENT DOCUMENTS

| 0 178 826 | 4/1986 | European Pat. Off. . |
| 2 255 092 | 10/1992 | United Kingdom . |
| WO 92/08703 | 5/1992 | WIPO . |

OTHER PUBLICATIONS

E. Schmitz & I. Eichhorn, *Acetals and hemiacetals*, Chemistry of the Ether Linkage, Chapter 7, 337.

W.J. Croxall & M.F. Fegley, *Chlorine Derivatives of, Certain β–Ethoxy Esters*, J. Amer. Chem. Soc., 2888–2890 (Jul.1950).

D.B. Killian et al., *The Preparation of Some α–Unsaturated Ethers from 2,2–Dimethoxyalkanes*, 57 J. Amer. Chem. Soc., 544–545 (1935).

J. Leonard et al., *Highly Selective Stereochemically Controlled Five–versus Six–membered Acetal Ring Cyclisation*, J. Chem. Soc., Chem Commun., 23–25, (1993).

S. Antus et al., *Alkali–catalysed Alkoxy Exchange, Alcohol Elimination, and Hydrolysis of Acetals Having a Dissociable α–Proton*, J. Chem. Soc., Chem Commun., 333–334 (1977).

S. Antus, *Alkalilabilität von in 2–Stellung anionisch aktiverten Acetalen*, Liebigs Ann. Chem., 107–117 (1978).

A. Tökés and S. Antus, *Oxidative Rearrangement of 2'–Acetamidochalcones with Thallium (III) Nitrate: A New Route to 3–Aryl–4(1H)–quinolones*, Liebigs Ann. Chem., 927–929 (1993).

G. Gross et al., *Chemical Synthesis of α–Formylphenylacetic Acid, the Postulated Precursor of Tropic Acid*, 36 Z. Naturforsch, 611–614 (1981).

R. Eade et al. *C–Glycosylflavonoids. The Synthesis of 7,4'Di–0–methylpuerarin (*–C–β–D–Glucopyranosyl–74, '–dimethoxyisoflavone)*, Aust. J. Chem, 2699–2706 (1978).

*Primary Examiner*—John M. Ford
*Attorney, Agent, or Firm*—Thomas R. Savitsky

[57] ABSTRACT

A process for preparing agrochemical intermediates of formula (I), wherein W is $(CH_3O)_2CH.CHCO_2CH_3$ or $CH_3O.CH=CCO_2CH_3$; $Z^1$ is a halogen atom; and $R^1$, $R^2$, $R^3$ and $R^4$ are independently hydrogen, halogen, $C_{1-4}$ alky, C alkoxy, acetoxy or acyl; the process comprising the steps of: (a) reacting a compound of formula (II), wherein X, $R^1$, $R^2$, $R^3$ and $R^4$ are as defined above, with a compound of formula $ROCH_3$, wherein R is a metal; and, (b) reacting the product of (a) with a compound of formula (III), wherein $Z^1$ and $Z^2$ are halogen atoms. A process for the preparation of compounds of formula (II) and compounds of formula (II) themselves. A process for obtaining, in substantially pure form, a compound of formula (11) and compounds of formula (II) themselves. A process for obtaining, in substantially pure form, a compound of formula (11) wherein $R^1$, $R^2$, $R^3$ and $R^4$ are all hydrogen.

6 Claims, No Drawings

PROCESS FOR THE PREPARATION OF PYRIMIDINE COMPOUNDS

The present invention relates to a process for preparing (E)-methyl 2-[2-(6-chloropyrimidin-4-yloxy)phenyl]-3-methoxypropenoate, an intermediate in the agrochemical industry.

Methods for preparing (E)-methyl 2-[2-(6-chloropyrimidin-4-yloxy)phenyl]-3-methoxypropenoate are described in WO 92/0870.

The present invention provides a process for preparing a compound of formula (I), comprising treating a compound of formula (II) with an acid catalyst in the presence of an acid anhydride, an acid chloride or 2-acetoxybenzonitrile at a temperature in the range 70–110° C.

Acid catalysts include acids (such as sulphonic acid or a derivative thereof (for example chlorosulphonic acid, methane sulphonic acid or p-toluene sulphonic acid), hydrochloric acid or an acetic acid derivative (for example trifluoroacetic acid or di- or trichloroacetic acid)), a suitable phenol derivative (such as 2-cyanophenol) or potassium bisulfate.

Acid anhydrides are preferably $C_{2-5}$ alkyl anhydrides, for example acetic anhydride.

Acid chlorides are preferably $C_{2-5}$ alkyl chlorides, for example acetyl chloride or propionyl chloride.

The process of the invention can be carried out in the presence of a solvent. Such a solvent is preferably inert under the process conditions. Suitable solvents include saturated or unsaturated hydrocarbons (such as toluene, o-xylene, m-xylene, p-xylene, cyclohexane or methylcyclohexane), an ether (such as glyme or diglyme) or a ketone (such as methylisobutylketone). It is preferred that the solvent has a boiling point in the range 70–140° C., especially in the range 85–120° C.

In one aspect the present invention provides a process for preparing a compound of formula (I), comprising treating a compound of formula (II) with an acid catalyst in the presence of an acid anhydride.

In another aspect the present invention provides a process for preparing a compound of formula (I), comprising treating a compound of formula (II) with methane sulphonic acid, chlorosulphonic acid or 2-cyanophenol in the presence of an acid anhydride, an acid chloride or 2-acetoxybenzonitrile, the process being conducted in the presence of a solvent.

In a further aspect the present invention provides a process for preparing a compound of formula (I), comprising treating a compound of formula (II) with methane sulphonic acid or chlorosulphonic acid in the presence of an acid anhydride, the process being conducted in the presence of a solvent.

The process of the present invention can be carried out by treating a compound of formula (II) with an acid catalyst (preferably methane sulphonic acid) in the presence of an acid anhydride (especially acetic anhydride), an acid chloride (especially acetyl chloride) or 2-acetoxybenzontrile at a temperature in the range 70–110° C. (especially 85–100° C.) at ambient pressure.

Alternatively, the process of the present invention can be carried out by treating a compound of formula (II) with an acid catalyst (preferably methane sulphonic acid) in solvent (especially toluene or methylcyclohexane) in presence of a suitable acid anhydride (especially acetic anhydride) at a temperature in range 70–110° C. (especially 85–100° C.) at ambient pressure.

In a further aspect the present invention provides a process for preparing a compound of formula (I) comprising treating a compound of formula (II) (1 equivalent) with methane sulphonic acid (about 0.05 equivalents) in the presence of acetic anhydride (about 1 equivalent, preferably 1 to 1.1 equivalents) at a temperature in the range 85–105° C. (especially 90–95° C.), the process being carried out in the absence of a solvent.

It is preferred that, when the process is carried out in the absence of a solvent, the compound of formula (I) is isolated by: (i) distilling off by-products (preferably at a temperature in the range 50–150° C. and under atmospheric pressure), (ii) partitioning the resulting residue between an organic solvent (such as toluene or a xylene) and water, and (iii) evaporating the organic phase to leave a compound of formula (I).

The following Examples illustrate the invention. Throughout the Examples the following abbreviations are used:

gc=gas chromatography NMR=nuclear magnetic resonance

EXAMPLE 1

Methyl 2-[2-(6-chloropyrimidin-4-yloxy)phenyl]-3,3-dimethoxypropanoate (44.8 g) was heated to 95° C. 2-Cyanophenol (14.3g) was added and acetic anhydride (11.7 g) was added via a syringe pump running at 6.35 ml $h^{-1}$. The reaction was monitored by gc and $^1H$ NMR, which showed that demethanolysis was complete in 4 hours.

EXAMPLE 2

Methyl 2-[2-(6-chloropyrimidin-4-yloxy)phenyl]-3,3-dimethoxypropanoate (44.6 g) was heated to 90–95° C. 2-Acetoxybenzonitrile (19.3 g) was added and then methane sulphonic acid (0.61 g) was added via a syringe. The reaction was monitored by gc and $^1H$ NMR, which showed that demethanolysis was complete in 5 hours.

EXAMPLE 3

A mixture of methyl 2-[2-(6-chloropyrimidin-4-yloxy)phenyl]-3,3-dimethoxypropanoate (17.98 g), acetic anhydride (5.16 g) and toluene (73 ml) was stirred at 90° C. for 20 minutes. Methane sulphonic acid (0.49 g) was added to the mixture and the mixture was heated at 90° C. for 1 hour. The mixture was cooled to room temperature, washed with cold water (25 ml) and with hot (50° C.) water (2×25 ml). The organic layer was evaporated at 75° C. (initially on a rotary evaporator, then at circa 15 mm Hg) to leave (E)-methyl 2-[-(6-chloropyrimidin-4-yloxy)phenyl]-3-methoxypropenoate as a solid (16.1 g).

EXAMPLE 4

Preparation of Starting Material

To a stirred mixture of 3-(α-methoxy)methylenebenzofuran-2(3H)-one (193.4 g of 91% pure material) and 4,6-dichloropyrimidine (165.5 g) in methyl formate (400 g) at 20–25° C. under nitrogen was added sodium methoxide (207 g of a 30% w/w solution in methanol) portionwise, over 10 hours while maintaining the temperature at 20–25° C. Once all the sodium methoxide solution had been added the reaction mixture was stirred for 2 hours after which water (9 g) was added. The methanol and methyl formate were distilled from the reaction mixture (internal temperature 90–95° C.) to leave a residue.

Water (700 g) was added to the residue and the mixture stirred at 80° C. for 30 minutes.

Methylcyclohexane (400 g) was added at 65° C., the temperature adjusted to 70° C. and the mixture stirred for a further 30 minutes before being allowed to settle for 30 minutes. The aqueous layer was separated and the organic phase washed at 70° C. with aqueous potassium hydroxide (400 g of a 3% solution) and aqueous hydrochloric acid (80 g of a 1% solution). Each wash was stirred for 30 minutes and allowed to settle for 30 minutes prior to separation. The methylcyclohexane solution was cooled to 25° C., stirred for 30 minutes and allowed to settle for 1 hour. A two phase system was obtained, a lower layer comprising:

(E)-methyl 2-[2-(6-chloropyrimidin-4-yloxy)phenyl]-3-methoxypropenoate 7.28%
methyl 2-[2-(6-chloropyrimidin-4-yloxy)phenyl]-3,3-dimethoxypropanoate 63.5%
methylcyclohexane 15–20% and an upper layer comprising:

(E)-methyl 2-[2-(6-chloropyrimidin-4-yloxy)phenyl]-3-methoxypropenoate 1.4%
methyl 2-[2-(6-chloropyrimidin-4-yloxy)phenyl]-3,3-dimethoxypropanoate 11.4%
methylcyclohexane 80–85%

The upper layer was retained for use in future reactions.

Solvent was removed from the lower layer by distillation at 50 mm Hg at a gradually increasing temperature until 90° C. was achieved. The mixture was held at 90° C. for 30 minutes. After this time the pressure was reduced to 5–10 mm Hg and the temperature increased to 120° C. during which time chloromethoxypyrimidine distilled. [The condenser coolant was at 35–40° C.] The mixture is held at 120° C. until analysis showed that the level of chloromethoxypyrimidine was acceptable.

A sample comprising methyl 2-[2-(6-chloropyrimidin-4-yloxy)phenyl]-3,3-dimethoxypropanoate (230.7 g) and (E)-methyl 2-[2-(6-chloropyrimidin-4-yloxy)phenyl]-3-methoxypropenoate (21 g) prepared by a method analogous to the above was heated to 90–95° C. Acetic anhydride (74.2 g) and methane sulphonic acid (1.75 g) were added sequentially with stirring. The resulting mixture was heated at 90–95° C. for 2 hours to leave (E)-methyl [2-(6-chloropyrimidin-4-yloxy)-phenyl]-3-methoxypropenoate (216.9 g).

Chemical Structures (in description)

(I)

(II)

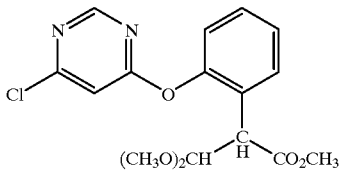

What is claimed is:

1. A process for preparing a compound of formula (I):

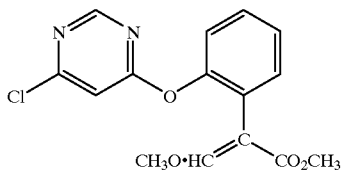

comprising treating a compound if formula (II)

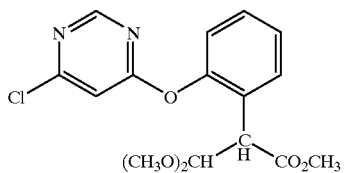

with an acid catalyst in the presence of an acid anhydride, an acid chloride or 2-acetoxybenzonitrile at a temperature in the range of 70–110° C.; provided that when the acid catalyst is p-toluene sulphonic acid or potassium bisulphate then the process is conducted in the presence of an acid anhydride.

2. A process as claimed in claim 1 wherein the acid catalyst is methane sulphonic acid, chlorosulphonic acid or 2-cyanophenol.

3. A process as claimed in claim 2 which is conducted in the presence of a solvent.

4. A process as claimed in claim 1 wherein a compound of formula (II) is treated with methane sulphonic acid or chlorosulphonic acid in the presence of an acid anhydride, the process being conducted in the presence of a solvent.

5. A process as claimed in claim 1 wherein a compound of formula (II) is treated with methane sulphonic acid in the presence of acetic anhydride at a temperature in the range 85–105° C., the process being conducted in the absence of a solvent.

6. A process as claimed in claim 5 wherein the ratio of compound of formula (II):

methane sulphonic acid: acetic anhydride is about 1:0.05:1 equivalents.

* * * * *